United States Patent [19]

Henrie, II et al.

[11] Patent Number: 4,787,931
[45] Date of Patent: Nov. 29, 1988

[54] N-PHENYL-N'-(PYRIDINYL-N-OXIDE)UREA PLANT REGULATORS

[75] Inventors: Robert Henrie, II, E. Windsor; Christine M. Green, Skillman, both of N.J.; Robert E. Sticker, Middleport, N.Y.

[73] Assignee: FMC Corporation, Philadelphia, Pa.

[21] Appl. No.: 875,415

[22] Filed: Jun. 17, 1986

Related U.S. Application Data

[63] Continuation-in-part of Ser. No. 586,574, Mar. 6, 1984, abandoned, which is a continuation-in-part of Ser. No. 480,055, Mar. 29, 1983, abandoned.

[51] Int. Cl.⁴ .................. A01N 43/40; C07D 213/75
[52] U.S. Cl. ........................ 71/94; 546/306; 546/257; 546/258
[58] Field of Search .................. 71/94; 546/306, 257, 546/258

[56] References Cited

U.S. PATENT DOCUMENTS

| | | | |
|---|---|---|---|
| 4,063,928 | 12/1977 | Johnston | 71/94 |
| 4,279,639 | 7/1981 | Okamoto et al. | 71/94 |
| 4,308,054 | 12/1981 | Isogai et al. | 71/94 |
| 4,358,606 | 11/1982 | Lee et al. | 71/94 |
| 4,367,339 | 1/1983 | O'Neal et al. | 71/94 |
| 4,473,395 | 9/1984 | Hawkins et al. | 71/94 |

FOREIGN PATENT DOCUMENTS

1147438  4/1969  United Kingdom.

OTHER PUBLICATIONS

Katritzky, J. Chem. Soc., 191–197 (1957).
Isogai, Chemical Regulation in Plants, 17, 27–43, 1982.

*Primary Examiner*—Jane T. Fan
*Attorney, Agent, or Firm*—H. Robinson Ertelt; Robert L. Andersen; William Schmonsees

[57] ABSTRACT

N-phenyl-N'-(pyridinyl-N-oxide)ureas of the formula

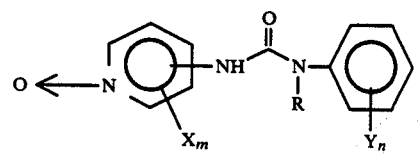

and their use as plant regulators are disclosed and exemplified.

22 Claims, No Drawings

N-PHENYL-N'-(PYRIDINYL-N-OXIDE)UREA PLANT REGULATORS

This application is a continuation-in-part of U.S. Ser. No. 586,574, filed Mar. 6, 1984, now abandoned, which is a continuation-in-part of U.S. Ser. No. 480,055, filed Mar. 29, 1983, now abandoned.

The present invention relates to N-phenyl-N'-(pyridinyl-N-oxide)ureas as plant regulators for agricultural crops such as wheat, corn, cotton, soybean and the like, to novel compositions thereof, and to a method for regulating growth and development of agricultural crops.

Substantial research efforts have been devoted to finding new chemical compounds which exhibit cytokinin-like hormonal activity in agricultural crops. Such activity can beneficially affect the course of plant development in many ways. For example it can accelerate plant growth, modify plant growth or development in such a way as to increase yield, ensure flowering or fruiting at a desired period in time, prevent or promote abscission, i.e., the falling of fruit or flowers from plants, increase the weight of leaves or stalks, retard senescence of the plant, and/or exhibit various other properties desirable in the growth and development of various plants. Compounds which perform such functions are commonly known as "plant regulators" and are hereinafter referred to by that term.

Typical compounds which have exhibited plant regulator activity include 6-benzyladenine, kinetin, and 4-pyridylphenylurea. U.S. Pat. No. 4,193,788 discloses the use of certain N-(2-chloro-4-pyridyl)ureas as plant regulators. Likewise U.S. Pat. Nos. 4,279,639 and 4,308,054 disclose various other N-(2- and/or 6-substituted-4-pyridyl)-N'-(optionally substituted phenyl)ureas as plant regulators.

While the foregoing patents describe only pyridylureas in which the pyridyl group is attached at the 4-position, certain other pyridylureas in which the pyridyl group is attached at the 2- and 3-position also exhibit some cytokinin-like activity. See, for example, Bruce, M. I. and Zwar, J. A., "Cytokinin Activity of Some Substituted Ureas and Thioureas", Proc. Roy. Soc. (London) 1966, pp. 245–265. The prior art does not teach or suggest the use of pyridinyl N-oxides as plant regulators.

The N-oxides of this invention exhibit improved anti-senescence performance over the unoxidized analogs. For some compounds this improvement is manifested by a greater than 100% increase in chlorophyll retention. Alternatively, the N-oxides may be used at significantly lower concentrations than the unoxidized compounds to achieve equivalent chlorophyll retention.

As used throughout the following description and claims the terms "halogen" and "halo" mean halogen atoms selected from bromine, chlorine, fluorine and iodine, preferably bromine, chlorine and fluorine. The term "lower alkyl" means methyl, ethyl, or propyl.

In accordance with the foregoing, the present invention comprises plant regulators of the formula

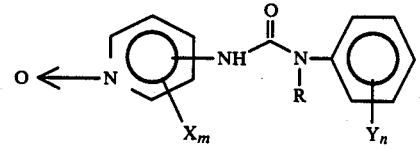

in which R is hydrogen or a lower alkyl group, and
(a) the pyridinyl ring is attached at position 4; each X group is independently selected from halogen, $(C_{1-6})$haloalkyl, $(C_{1-4})$alkyl $(C_{1-5})$alkoxy, $(C_{1-2})$alkoxycarbonyl, aminocarbonyl, $(C_{1-4})$alkylamino, di$(C_{1-2})$alkylamino, di$(C_{1-2})$alkylaminocarbonyl, di$(C_{1-2})$alkylamino-N-oxide, $(C_{1-2})$alkylthio, $(C_{1-2})$alkylsulfonyl, pyridinyl, phenylthio, phenylsulfonyl, phenyl, or benzylamino in which the aromatic ring is in turn unsubstituted or substituted with 1 to 5 halogen atoms; each Y group is independently selected from halogen, $(C_{1-2})$alkyl, $(C_{1-2})$alkoxy, $(C_{1-2})$alkylthio, $(C_{1-2})$alkylsulfonyl, hydroxyl, or trihalomethyl; m is 0, 1 or 2; and n is 0 to 5; or
(b) the pyridinyl ring is attached at position 3; X is chloro, methoxy or an acetylmethylamino group; Y is halogen; m is 0 or 1; and n is 0 or 1.

Specific compounds of this invention and their physical constants are shown in Table 1 below.

The composition aspect of the present invention provides a composition containing a plant regulating amount of the compounds described herein in admixture with an agriculturally acceptable carrier, diluent, extender or adjuvant.

In the composition aspect of this invention, the plant regulator compounds of this invention, like most agricultural chemicals, are generally not applied full strength, but are formulated with agriculturally acceptable carriers normally employed for facilitating the dispersion of active ingredients, various additives, and optionally with other active ingredients, recognizing that the formulation and mode of application of the active component may affect the activity of the material. The present compounds may be applied, for example, as powders or liquids, the choice of application varying with the plant species and environmental factors present at the particular locus of application. Thus, the compounds may be formulated as emulsifiable concentrates, as wettable powders, as flowable formulations, as solutions, as dispersions, as suspensions and the like.

The plant regulators of this invention are suitably employed in a number of broad-leafed and grain crops, for example, soybean, lima bean, wheat, rice, corn, sorghum, and cotton, and turf grasses to name a few. In soybean, the compounds of the invention retard senescence and increase yields. In wheat, they retard senescence and exert an antilodging effect. In cotton, the compounds of the invention improve leaf abcission. In turf grasses, the compounds retard growth rate.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of exemplary types of formulations which may be employed for dispersion of the plant regulators of the present invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

The following are specific examples of emulsifiable concentrate formulations suitable for use in the present invention:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Wettable powders, also useful formulations for plant regulators, are in the form of finely divided particles which disperse readily in water or other liquid vehicles. The wettable powder is ultimately applied to the plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp < 100° C.) are suitably formulated in the concentration range of 5 to 50% by weight, usually from 10 to 30%; high melting solids (mp > 100° C.) being formulated in the range of 5 to 95% by weight, usually 50 to 85%. An agriculturally acceptable carrier or diluent, frequently including a small amount of a surfactant to facilitate wetting dispersion and suspension, accounts for the balance of the formulation.

The following are specific examples of wettable powder formulations suitable for use in the present invention:

| Component: | % by Wt. |
|---|---|
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Flowable formulations are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations suitable for use in the present invention:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylinic alcohols | 2.50 |
| Xanthan gum | 0.08 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylinic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively nonvolatile solvent such as water, corn oil, kerosene, propylene glycol, or other suitable solvents. This type of formulation is particularly useful for ultra low volume application.

The following illustrate specific suspensions which are suitable for use in the present invention:

| Oil Suspension: | % by Wt. |
| --- | --- |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

The concentration of the compound in use dilution is normally in the range of about 2% to about 0.1%. Many variations of spraying and dusting compositions in the art may be used by substituting or adding a compound of this invention into compositions known or apparent to the art.

The compositions may be formulated and applied with other suitable active ingredients, including nematicides, insecticides, acaricides, fungicides, other plant regulators, herbicides, fertilizers, etc.

In applying the foregoing chemicals, an effective growth regulating amount of the active ingredient must be applied. While the application rate will vary widely depending on the choice of compound, the formulation and mode of application, the plant species being treated and the planting density, a suitable use rate may be in the range of 0.01 to 10 kg/hectare, preferably 0.05 to about 5 kg/hectare.

The compounds of this invention may be prepared by heating an aminopyridine and a substituted phenyl isocyanate in a solvent such as 2-butanone, toluene, or methylene chloride to produce the corresponding N-pyridinylurea. The N-pyridinylurea is then treated with a suitable oxidizing agent, for example meta-chloroperoxybenzoic acid (MCPBA) in a solvent such as ethanol or ethyl acetate to produce the corresponding (pyridinyl-N-oxide)urea.

The following examples illustrate preparation of the compounds of this invention.

EXAMPLE 1

Synthesis of N-Phenyl-N'-(3-pyridinyl-N-oxide)urea

Under a dry nitrogen atmosphere a mixture of 2.13 g (0.01 mole) of N-phenyl-N'-(3-pyridinyl)urea and 1.9 g (0.011 mole) of m-chloroperoxybenzoic acid in 40 ml of ethanol was stirred at room temperature. The product precipitated and was filtered from the reaction mixture. The filter cake was washed with a small amount of ethanol and dried to yield 2.26 g of N-phenyl-N'-(3-pyridinyl-N-oxide)urea (m.p. 220° C.).

Analysis calc'd for $C_{12}H_{11}N_3O_2$: C 62.87; H 4.84; N 18.33; Found: C 63.15; H 4.71; N 18.55.

NMR (trifluoroacetic acid): 7.43(s,5H); 7.77–8.63 (m,3H); 9.63 (bt,1H).

EXAMPLE 2

Synthesis of N-Phenyl-N'-(4-pyridinyl-N-oxide)urea

In a manner similar to Example 1, 1.0 g (0.0047 mole) of N-phenyl-N'-4-pyridinylurea and 1.09 g (0.0054 mole) of m-chloroperoxybenzoic acid in 100 ml of ethyl acetate produced 0.87 g of N-phenyl-N'-(4-pyridinyl-N-oxide)urea (m.p. 235° C. dec.).

Analysis calc'd for $C_{12}H_{11}N_3O_2$: C 62.87; H 4.84; N 18.33; Found: C 62.98; H 5.05; N 17.78.

NMR (dimethylsulfoxide-$d_6$, trifluoroacetic acid): 7.00–7.70 (m,7H); 7.98–8.10(d,3H).

EXAMPLE 3

Synthesis of N'-(2-chloro-4-pyridinyl-N-oxide)-N-phenylurea

In a manner similar to Example 1, 3.3 g (0.013 mole) of N'-(2-chloro-4-pyridinyl)-N-phenylurea and 3.0 g (0.014 mole) of m-chloroperoxybenzoic acid in 50 ml of ethanol produced 1.8 g of N'-(2-chloro-4-pyridinyl-N-oxide)-N-phenylurea (m.p. 183° C. dec.).

Analysis calc'd for $C_{12}H_{10}ClN_3O_2$: C 54.66; H 3.82; N 15.94; Found: C 55.11; H 4.11; N 16.14.

NMR (dimethylsulfoxide-$d_6$): 7.00–7.80(m,6H); 7.93–7.98(d,1H); 8.27–8.38(d,1H); 8.97(s,1H); 9.35(s,1H).

Compound Numbers 1–22, 24, 25, 27 and 28 of Table I were prepared by the foregoing methods. The examples set forth below illustrate other methods of preparation of compounds of the invention.

EXAMPLE 4

Synthesis of N'-(2,6-dichloro-4-pyridinyl-N-oxide)-N-(3-fluorophenyl)urea

Step A

Methyl 2,6-dichloroisonicotinate N-oxide

A stirred mixture of 15.3 g (0.073 mole) of methyl 2,6-dichloroisonicotinate in 180 ml of trifluoroacetic acid was heated at 90° C. During a six hour period 34 ml of 30% hydrogen peroxide was added to the hot reaction mixture in four to five ml aliquots. After complete addition the reaction mixture was stirred at 90° C. for two hours. The solvent was distilled from the mixture under reduced pressure to leave a solid. The solid was triturated with water, and the mixture was then filtered. The filter cake was recrystallized from acetone to yield 8.75 g of methyl 2,6-dichloroisonicotinate N-oxide.

Step B 2,6-Dichloro-4-pyridinecarboxylic acid Hydrazide 1-Oxide

To a cold stirred mixture of 8.75 g (0.039 mole) of methyl 2,6-dichloronicotinate N-oxide in 50 ml of methanol was added dropwise 2.0 g (0.063 mole) of hydrazine in 14 ml of methanol. After complete addition the mixture was stirred for one hour then placed in a freezer for approximately 18 hours. The solvent was then removed by distillation under reduced pressure to leave a solid. The solid was stirred in isopropanol then filtered. The filter cake was added to 75 ml of refluxing ethanol and the resulting mixture filtered hot to yield 4.3 g of 2,6-dichloro-4-pyridinecarboxylic acid hydrazide 1-oxide as a solid.

Step C 2,6-Dichloro-4-pyridinecarbonyl Azide 1-Oxide

To a stirred 0° C. mixture of 2.0 g (0.009 mole) of 2,6-dichloro-4-pyridinecarboxylic acid hydrazide 1-oxide and 0.78 g (0.011 mole) of sodium nitrite in 7 ml of diethyl ether and 13 ml of water was added 12 ml of 1N hydrochloric acid. AAfter complete addition the mixture was stirred for 45 minutes at which time the mixture was extracted with three 100 ml portions of diethyl ether. The extracts were combined, dried over anhydrous sodium sulfate, and filtered. The filtrate was evaporated under reduced pressure to leave 2.2 g of 2,6-dichloro-4-pyridinecarbonyl azide 1-oxide as a solid.

Step D

N'-(2,6-Dichloro-4-pyridinyl-N-oxide)-N-(3-fluorophenyl)urea

To a stirred mixture of 0.5 g (0.0021 mole) of 2,6-dichloro-4-pyridinecarbonyl azide 1-oxide in 15 ml of toluene was added 0.77 g (0.0069 mole) of 3-fluoroaniline. After complete addition the mixture was stirred at room temperature for two days, then at 95° C. for approximately 22 hours. The reaction mixture was cooled and the solvent removed by evaporation under reduced pressure to leave a residue. The residue was dissolved in ethyl acetate and filtered. The filtrate was evaporated under reduced pressure to yield 0.2 g of N'-(2,6-dichloro-4-pyridinyl-N-oxide)-N-(3-fluorophenyl)urea as a solid (mp 253°–255° C. dec.), Compound 23 of Table 1.

Analysis calc'd for $C_{12}H_8N_3O_2C_{12}F$: C 45.59; H 2.55; N 13.29; Found: C 45.76; H 2.58; N 12.55.

NMR (trifluoroacetic acid): 6.90–7.50 (m,4H); 8.17 (s,2H).

EXAMPLE 5

Synthesis of N-(3-Fluorophenyl)-N'-(2-methyl-4-Pyridinyl-N-oxide)urea

Step A

4-Amino-2-methylpyridine N-oxide

Hydrogenation of 6.02 g (0.39 mole) of 2-methyl-4-nitropyridine N-oxide in the presence of 0.26 g of 10% palladium on carbon in 6 ml of glacial acetic acid and 150 ml of absolute ethanol produced a residue. The residue was dissolved in 50 ml of water. The aqueous solution was neutralized with sodium bicarbonate then diluted with a saturated aqueous sodium chloride solution until a volume of 250 ml was obtained. The resultant solution was extracted with 200 ml of methylene chloride in a continuous extraction apparatus for approximately 18 hours. The aqueous phase was evaporated to dryness under reduced pressure to leave an orange solid. The solid was subjected to column chromatography on silica gel, eluted first with methanol:chloroform (20:80), then with methanol:chloroform (25:75), to give an oily solid. The oily solid was stirred in 100 ml of acetone and the resultant mixture placed in a refrigerator for three days. The mixture was filtered and the filter cake rinsed with fresh acetone to yield 2.0 g of 4-amino-2-methylpyridine N-oxide.

Step B

N-(3-Fluorophenyl)-N'-(2-methyl-4-pyridinyl-N-oxide)urea

A mixture of 0.53 g (0.043 mole) of 4-amino-2-methylpyridine N-oxide and 0.6 ml (0.53 mole) of 3-fluorophenylisocyanate in 25 ml of pyridine was stirred at room temperature for two weeks. The solvent was evaporated from the mixture under reduced pressure to leave a solid. The solid was triturated with 100 ml of ethyl acetate, then the mixture was filtered. The filter cake was rinsed with ethyl acetate, and dried under reduced pressure at 40° C. The dry solid was dissolved in 50 ml of absolute methanol and the solution heated and stirred with decolorizing carbon. The mixture was filtered while hot through a pad of celite, yielding an orange filtrate. The filtrate was evaporated under reduced pressure to a volume of about two milliliters. Diethyl ether was added until a precipitate formed. The solvents were removed by evaporation under reduced pressure to leave a solid residue. The solid residue was purified by recrystallization from a mixture of 50 ml of water and 2 to 3 ml of ethanol to yield 0.14 g of N-(3-fluorophenyl)-N'-(2-methyl-4-pyridinyl-N-oxide)urea (mp >250° C.), Compound 26 of Table I.

NMR (dimethylsulfoxide-$d_6$): 2.37(s,3H); 6.70–7.60 (m,6H); 8.12–8.23 (d,1H); 9.20(bs 2H).

EXAMPLE 6

Synthesis of N'-(2-carboxamido-4-pyridinyl-N-oxide)-N-phenylurea

A stirred solution of 1.0 g (0.036 mole) of N'-(2-carbomethoxy-4-pyridinyl-N-oxide)-N-phenylurea (Compound 28) in 250 ml of absolute methanol was cooled to 0° C. Anhydrous ammonia gas was bubbled into the solution for approximately 30 minutes at which time the reaction mixture was allowed to warm to room temperature and stir for approximately 18 hours. The solvent was evaporated from the mixture under reduced pressure to leave a solid. The solid was purified by recrystallization from ethanol to yield 0.57 g of N'-(2-carboxamido-4-pyridinyl-N-oxide)-N-phenylurea (mp 241°–243° C. dec), Compound 29 of Table I.

NMR (trifluoroacetic acid): 7.37(bs,5H); 8.03–8.22 (dd,1H); 8.53–8.67(d,1H); 8.95–9.00(d,1H).

EXAMPLE 7

Synthesis of N'-[2-(Dimethylamino-N-oxide)-4-pyridinyl-N-oxide]-N-phenylurea

Step A

N'-(2-Dimethylamino-4-pyridinyl-N-oxide)-N-phenylurea

A solution of 2.1 g (0.080 mole) of N'-(2-chloro-4-pyridinyl-N-oxide)-N-phenylurea (Compound 7) and 20 ml of a 40% aqueous dimethylamine solution in 20 ml of dimethylsulfoxide was stirred at room temperature for two days. The reaction mixture was placed in a freezer for several hours then filtered. The filter cake was washed with water then dried at 50° C. under reduced pressure to yield 1.63 g of N'-(2-dimethylamino-4-pyridinyl-N-oxide)-N-phenylurea (mp 208°–209° C. dec), Compound 30 of Table I.

NMR (dimethylsulfoxide-$d_6$): 2.95(s,6H); 6.90–7.60 (m,7H); 7.93–8.05(d,1H); 8.90(bs,1H); 9.10(bs,1H).

Step B

N'-[2-(Dimethylamino-N-oxide)-4-pyridinyl-N-oxide]-N-phenylurea

Under a dry nitrogen atmosphere a mixture of 0.51 g (0.019 mole) of N'-(2-dimethylamino-4-pyridinyl-N-oxide)-N-phenylurea and 0.78 g (0.0038 mole) of m-chloroperoxybenzoic acid in 35 ml of methanol was stirred at room temperature. The product precipitated and was filtered from the reaction mixture. The filter cake was washed with a small amount of cold methanol and dried to yield 0.37 g of N'-[2-(dimethylamino-N- oxide)-4-pyridinyl-N-oxide]-N-phenylurea (mp 186°–185° C. dec), Compound 31 of Table I.

Analysis calc'd for $C_{14}H_{16}N_4O_3$: C 58.32; H 5.59; N 19.43; Found: C 57.75; H 5.25; N 19.15.

NMR (trifluoroacetic acid): 4.23(s,3H); 7.37(bs,5H); 7.72–7.88(dd,1H); 8.60–8.73 (d,1H); 9.03–9.08(d,1H).

EXAMPLE 8

Synthesis of N'-(2-Methylsulfonyl-4-pyridinyl-N-oxide)-N-phenylurea

Step A

N'-(2-Methylthio-4-pyridinyl-N-oxide)-N-phenylurea

Under a dry nitrogen atmosphere a solution of 2.0 g (0.0076 mole) of N'-(2-chloro-4-pyridinyl-N-oxide)-N-phenylurea (Compound 7) and 0.8 g (0.0114 mole) of sodium methylthiolate in 35 ml of dimethylsulfoxide was stirred at room temperature for approximately 19 hours. The reaction mixture was poured into 200 ml of water to form a precipitate. The solid was collected by filtration, rinsed with water, and dried. The solid was purified by column chromatography on silica gel, eluted with methanol:methylene chloride (10:90) to yield 1.7 g of N'-(2-methylthio-4-pyridinyl-N-oxide)-N-phenylurea as a solid (mp 223.5°–224.5° C. dec.), Compound 32 of Table I.

NMR (trifluoroacetic acid): 2.70(s,3H); 7.40–7.70 (m,6H); 8.13–8.18(d,1H); 8.33–8.47(d,1H).

Step B

N'-(2-methylsulfonyl-4-pyridinyl-N-oxide)-N-phenylurea

A stirred solution of 1.0 g (0.0036 mole) of N'-(2-methylthio-4-pyridinyl-N-oxide)-N-phenylurea in 150 ml of methanol:ethyl acetate (1:1) was heated at 50° C. To the warm solution was added 1.8 g (0.0091 mole) of m-chloroperoxybenzoic acid. After complete addition the mixture was stirred at 50° C. for three hours. The solvent was removed from the reaction mixture by evaporation under reduced pressure to leave a solid. The solid was purified by recrystallization from aqueous acetone to yield 0.63 g of N'-(2-methylsulfonyl-4-pyridinyl-N-oxide)-N-phenylurea (mp 232°–234° C. dec.), Compound 33 of Table I.

NMR (trifluoroacetic acid): 3.70(s,3H); 7.47(s,5H); 8.33–8.53(dd,1H); 8.68–8.73(d,1H); 8.73–8.83 (d,1H).

EXAMPLE 9

Synthesis of N'-(2-Chloro-4-pyridinyl-N-oxide)-N-(3-hydroxyphenyl)urea

Step A

Phenyl N-(2-chloro-4-pyridinyl)carbamate

Under a dry nitrogen atmosphere a solution of 12.0 ml (0.096 mole) of phenyl chloroformate in 300 ml of methylene chloride was added dropwise to a cold (0° C.) stirred solution of 10.2 g (0.079 mole) of 4-amino-2-chloropyridine and 16.5 ml (0.12 mole) of triethylamine in 300 ml of methylene chloride. After complete addition the reaction mixture was allowed to come to room temperature and stirred at room temperature for approximately 18 hours. The mixture was washed with three 100 ml portions of water followed by 100 ml of an aqueous saturated sodium chloride solution. The washed mixture was dried over anhydrous magnesium sulfate and filtered. The filtrate was subjected to column chromatography on silica gel, eluted with acetone:methylene chloride (4:96), to yield 7.4 g of phenyl N-(2-chloro-4-pyridinyl)carbamate as a solid.

Step B

Phenyl N-(2-chloro-4-pyridinyl-N-oxide) carbamate

In a manner similar to Example 1, 7.4 g (0.030 mole) of phenyl N-(2-chloro-4-pyridinyl) carbamate and 10.4 g (0.051 mole) of m-chloroperoxybenzoic acid in 500 ml of ethyl acetate produced 5.7 g of phenyl N-(2-chloro-4-pyridinyl-N-oxide)carbamate.

Step C

N'-(2-Chloro-4-pyridinyl-N-oxide)-N-(3-hydroxyphenyl)urea

A suspension of 1.0 g (0.0038 mole) of phenyl N-(2-chloro-4-pyridinyl-N-oxide) carbamate, 0.5 g (0.0046 mole) of 3-aminophenol, and 1.0 ml (0.017 mole) of triethylamine in 50 ml of acetonitrile was treated in an ultrasonic bath for 16 hours. The reaction mixture was transferred to a flask, diluted with 50 ml of diethyl ether, and was placed in a freezer for two hours. A precipitate formed and was collected by filtration to yield 0.75 g of N'-(2-chloro-4-pyridinyl-N-oxide)-N-(3-hydroxyphenyl)urea (mp 240°–250° C. dec.), Compound 61 of Table 1.

EXAMPLE 10

Synthesis of N'-(2-Chloro-4-pyridinyl-N-oxide)-N-(3-methylthiophenyl)urea

A stirred mixture of 1.5 g (0.0057 mole) of phenyl N-(2-chloro-4-pyridinyl-N-oxide)carbamate, 0.79 ml (0.0057 mole) of triethylamine, and 0.84 ml (0.0068 mole) of 3-(methylmercapto)aniline in 50 ml of tetrahydrofuran was heated at reflux for approximately 18 hours. The mixture was allowed to cool to room temperature. A precipitate had formed and was collected by filtration to yield 1.6 g of N'-(2-chloro-4-pyridinyl-N-oxide)-N-(3-methylthiophenyl)urea (mp 183°–184° C. dec.), Compound 73 of Table 1.

Further compounds of the invention include:

N-(4-chlorophenyl)-N'-(2,6-dimethyl-4-pyridinyl-N-oxide)urea

N-(3,4-dichlorophenyl)-N'-(2,6-dimethyl-4-pyridinyl-N-oxide)urea

N'-(2,6-dimethyl-4-pyridinyl-N-oxide)-N-phenylurea

N-(4-chlorophenyl)-N'-(2-methyl-4-pyridinyl-N-oxide)urea

N-(3,4-dichlorophenyl)-N'-(2-methyl-4-pyridinyl-N-oxide)urea

N-(2-fluorophenyl)-N'-(4-pyridinyl-N-oxide)urea

N-(4-fluorophenyl)-N'-(4-pyridinyl-N-oxide)urea

N-(3,5-difluorophenyl)-N'-(2-methyl-4-pyridinyl-N-oxide)urea

N-(3,5-difluorophenyl)-N'-(2,6-dimethyl-4-pyridinyl-N-oxide)urea

N'-(2-trifluoromethyl-4-pyridinyl-N-oxide)-N-phenylurea

N'-(2-pentafluoroethyl-4-pyridinyl-N-oxide)-N-phenylurea

[N'-(2,6-dimethyl-4-pyridinyl-N-oxide)-N-phenyl]-methylurea

[N-(2-methyl-4-pyridinyl-N-oxide)-N-phenyl]-methylurea.

The compounds of this invention were tested for growth regulator activity as described below.

Antisenescence Test A

For each test five leaves were excised from wheat seedlings (*Triticum aestivum* cv. Prodax or Northrup King) which had been grown in a growth chamber for eight days. The leaves were weighed and placed in vials containing a $10^{-4}$ to $10^{-9}$ molar aqueous or aqueous acetone solution of the test compound. The vials containing the wheat leaves were incubated in the dark at 30° C. for four days. For an active compound, there was a visible difference between the control (containing only water or acetone/water) and the treated leaves. The latter were still green whereas the control leaves were yellowed, indicating that they contained little chlorophyll.

To measure chlorophyll content, the incubated leaves were extracted with two 5 ml portions of (1) dimethylsulfoxide or (2) hot (65° C.) methanol. The absorbence (measured at 652 nm) of the resulting chlorophyll-containing extract was recorded. The following formula was used to determine the micrograms of chlorophyll per gram of fresh weight:

(a) Samples extracted with dimethylsulfoxide:

$$\frac{A_{652}}{\text{fresh weight}} \times 278 = \mu g \text{ chlorophyll/g fresh weight}$$

(b) Samples extracted with methanol:

$$\frac{A_{652}}{\text{fresh weight}} \times 299 = \mu g \text{ chlorophyll/g fresh weight}$$

The average value of ($\mu g$) chlorophyll/(g) fresh weight was then calculated using three replicates of each concentration. In the tests the chlorophyll content per gram fresh weight was determined at the beginning of the test (zero value) and at the end of the test. The relationship of the chlorophyll content at the beginning and end of the test was then calculated for the treated and untreated tests. That value, reported as "% of zero value" in Table 2, confirms that these compounds substantially retard loss of chlorophyll. Comparative data for the unoxidized parents of a few of the more efficacious compounds are also shown in Table 2 identified by use of the suffix "A" after the appropriate compound number.

Some of the compounds were similarly tested on excised soybean leaves. The results of these tests are shown in Table 3.

Antisenescence Test B

For each test five leaves were excised from wheat seedlings (*Triticum aestivum* cv. Northrup King) which had been grown in a growth chamber for eight days. The leaves were weighed and placed in vials containing a $10^{-4}$ to $10^{-9}$ molar aqueous or aqueous acetone solution of the test compound. The vials containing the wheat leaves were incubated in the dark at 30° C. for four days. For an active compound, there was a visible difference between the control (containing only water or acetone/water) and the treated leaves. The latter were still green whereas the control leaves were yellowed, indicating that they contained little chlorophyll.

To estimate chlorophyll content, the incubated leaves are subjected to a visual evaluation, with a numerical rating of 1 through 5 assigned based on the following scale:

| Visual Rating | % Chlorophyll Range |
|---|---|
| 1 | 0–25 |
| 2 | 26–50 |
| 3 | 51–75 |
| 4 | 76–99 |
| 5 | 100 |

Using the visual ratings, the percent chlorophyll content (% RCC) is calculated by means of the following equation:

$$\% RCC = \frac{R - C}{ZT - C} \times 100$$

where R=assigned visual rating, C=visual rating of control, and ZT=visual rating for zero time.

This test was used to evaluate the antisenescence performance of Compounds 57 through 75.

Protein Determination

The purpose of this test was to compare the protein content of treated vs. untreated wheat leaves. The wheat leaves were treated as described in the preceding test and were then incubated for five or six days. Following the incubation period the leaves were removed from the test solution, ground in distilled water, and centrifuged. Soluble proteins were precipitated from the supernatant using trichloroacetic acid, redissolved in 0.1M sodium hydroxide, then assayed by the method of Lowry et al., J. Biol. Chem., Vol. 193, 265-75 (1951) to ascertain the amount ($\mu g$) of protein per g of fresh weight. As shown in Table 4 the test compounds maintained a protein level several times that of the untreated control.

Survey of Plant Responses

Compounds 1, 3, 6, and 7 were sprayed at rates of 0.5, 2 and 8 kg/ha on plants approximately fourteen days after planting. The plants utilized were peanut, soybean, cotton, tomato and lima bean. Fourteen days after spraying, morphological changes indicative of plant regulator activity were recorded. Compounds 1 and 6 exhibited apical inhibition in soybean. Compound 7 exhibited apical inhibition and axillary stimulation in soybean and lima bean and apical inhibition in cotton.

Soybean Antisenescence Evaluation

Soybean plants (Variety Williams) maintained in a growth chamber were sprayed with test chemicals at rates corresponding to 0.0625 to 2.0 kg/hectare. The test chemicals were sprayed as 1:4 acetone:water solutions containing 0.10% (V/V) sorbitan monolaurate as an emulsifier and stabilizer, 5 replicates each test. The test chemicals were applied at one of the following stages of development.

| Stage | Definition |
|---|---|
| R4 | Full Pod Stage: Pod is ¾ inch long at one of the four uppermost nodes on the main stem with a fully developed leaf. |
| R5 | Beginning Seed Stage: Seed is ⅛ inch long in a pod at one of the four uppermost nodes on the main stem with a fully developed leaf. |
| R6 | Full Seed Stage: Pod contains a green |

-continued

| Stage | Definition |
|---|---|
| | seed that fills the pod cavity at one of the four uppermost nodes on the main stem with a fully developed leaf. |

The treated soybean plants were then returned to a growth chamber. At various times after treatment the leaves and pods of the plants were visually inspected for senescence, and rated on a scale of 0 to 5 as follows:

| Rating | Leaf Senescence | Pod Senescence |
|---|---|---|
| 0 | Leaves abscised | Pods abscised or shattered |
| 1 | Yellow, less than 25% green leaves | Pod less than 25% green more than 75% yellow or brown |
| 2 | 25-50% green, 50-75% yellow leaves | Pods 25-50% green, 50-75% yellow or brown |
| 3 | 50-75% green, 25-50% yellow leaves | Pods 50-75% green, 25-50% yellow or brown |
| 4 | 75-99% green leaves, less than 25% | Pods 75-99% green, less than 25% yellow |
| 5 | 100% green leaves | Pods 100% green |

Each replicate of each rate/stage combination was given both leaf and pod senescence ratings. The ratings for the five replicates for each combination are averaged to produce mean leaf and pod senescence ratings. The results, set forth in Table 5, illustrate the marked antisenescense activity of the compounds when applied at the R4, R5 and R6 stages.

Soybean Yield Assessment

The soybean plants used in the senescence evaluation described above were eeld in the growth chamber until they reached full maturity. The plants were then examined to determine the number of pods, number of seeds, total seed weight, and weight per 100 seeds. The raw data was subjected to statistical analysis using Duncan's Multiple Range Test to determine if treatment with the test chemicals had caused significant yield changes as compared with untreated controls.

The results, set forth in Table 5A, clearly show that, regardless of the stage at which they were applied, the test chemicals caused substantial increases in weight per seed, in total seed weight per plant, or both.

Antilodging Test

Antilodging is the ability of a crop to remain upright in wind and rain allowing harvesting machinery to collect the crop. To this end stunting and stem thickening are desirable traits. In these tests, Compound 7 was applied postemergence at 0.5, 2.0 and 8.0 kg/ha at the 0, 2nd and 3rd node stages. Twenty-four hours before treatment the tillers were cut off at soil level. After treatment, the plants were placed in the greenhouse and watered daily until full senescence. The stem height of each plant was measured in millimeters from the soil level to the bottom of the head. Stem strength was measured by holding a finger just under the seed head, lightly touching the plant stem. The plant was bent away from the finger approximately 45° then released. The force and speed at which the stem returned to the original position was noted on a scale of 1 to 5. A rating of 1 meant the plant moved only sightly, if at all; a rating of 5 meant the plant returned quickly to the original position with some spring in its return.

The antilodging exhibited by Compound 7 was pronounced in wheat at the 3rd node growth stage at application rates of 2.0 and 8.0 kg/ha.

Turf Reduction Test

Table 6 presents turf reduction data for Compound 7. Turf reduction, or the retardation of grass growth, is a desirable quality since it would mean the number of lawn cuttings could be reduced per season.

The test was carried out by spraying bluegrass (a mixture of Adelphi, Baron, Fylking, and Glade), which had been trimmed to 1" above the pot rim, with 5 ml of the appropriate test solution. The test solutions were prepared as follows:

| Test rate desired (kg/ha) | Acetone ml | Stock sol'n (ml) | Water (ml) | 10% aqueous Tween-20 ® (ml) |
|---|---|---|---|---|
| 2.0 | — | 25.0 | 25.0 | 0.5 |
| 1.0 | 12.5 | 12.5 | 25.0 | 0.5 |
| 0.5 | 18.75 | 6.25 | 25.0 | 0.5 |
| 0.25 | 21.87 | 3.13 | 25.0 | 0.5 |

Stock Solution = 72.0 mg Compound 7 in 50 ml acetone

Half of the treated pots were treated again after one week to provide data for a two treatment test. Forty-one days after initial treatment the grass growth average was measured by placing a measuring stick on the pot edge and measuring to a midpoint between the tallest and the shortest blades of grass for each of the five replicates and the control. One inch (2.5 cm) was then subtracted to give the average growth. After the 41 day test was read the grass in each pot was trimmed to one inch above the edge. Seventy-one days after initial treatment each pot was re-evaluated in the manner described above.

As shown in Table 6, Compound 7 provided the best control of grass growth after 41 days at 0.5, 1.0 and 2.0 kg/ha in both the one and two application tests.

Cotton Defoliation Test

This test was conducted by spraying 20 week old cotton plants (Stoneville 213, 1 plant per 641 pot) with 5 ml of test solution prepared as follows:

| Test rate desired (kg/ha) | Acetone ml | Tween-20/Water (ml) | Stock Sol'n (ml) |
|---|---|---|---|
| 0.25 | 4.37 | 20.00 | 0.63 |
| 0.50 | 3.75 | 20.00 | 1.25 |
| 1.0 | 2.5 | 20.00 | 2.50 |
| 2.0 | — | 20.00 | 5.00 |

Stock solution = 36.5 mg Compound 7 in 10 ml acetone
Tween-20/water = 1.25 ml 20% Tween-20 in water and 98.75 ml water Compound 7 proved to be an effective defoliant at the 2.0 and 1.0 kg/ha rate after two weeks.

TABLE 1

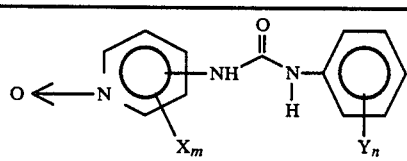

| Cpd. No. | Pyridinyl Position | Xm | Yn | Melting Point & NMR |
|---|---|---|---|---|
| 1 | 3 | H | H | See Example 1 |
| 2 | 3 | 6-Cl | H | 244–246° C. (dec.) (DMSO-$d_6$): 6.90–7.60(m,6H) 7.63–7.80(d,1H), 8.83–8.87(d,1H) 8.97(bs,1H) 9.13(bs,1H) |
| 3 | 3 | 6-OCH$_3$ | H | 215–216° C. (dec.) (DMSO-$d_6$): 3.93(s,3H) 6.90–7.60(m,7H) 7.59–7.60(d,1H) 8.82(bs,2H) |
| 4 | 3 | 2-Cl | H | 194–197° C. (dec.) (DMSO-$d_6$): 6.90–7.70(m,6H) 8.10–8.23(d,2H) 8.58(bs,1H) 9.55(bs,1H) |
| 5 | 3 | 6-N(CH$_3$)COCH$_3$ | H | 211° C. (dec.) (DMSO-$d_6$): 1.80(s,3H) 3.05(s,3H) 6.9–7.7(m,7H) 8.78–8.82(d,1H) 9.00(s,1H) 9.18(s,1H) |
| 6 | 4 | H | H | See Example 2 |
| 7 | 4 | 2-Cl | H | See Example 3 |
| 8 | 4 | 2-Cl | 3-F | 204° C. (dec.) (DMSO-$d_6$): 6.60–7.60(m,5H) 7.87–7.92(d,3H) 8.20–8.32(d,1H) 9.28–9.45(bs,2H) |
| 9 | 4 | 2-Cl | 3-Cl | 212–213° C. (dec.) |
| 10 | 4 | 2-NH(CH$_3$) | H | 243–246° C. (dec.) (trifluoroacetic acid-d): 3.13(s,3H) 6.70–6.87(dd,1H) 7.42(bs,5H) 7.52–7.57(d,1H) 7.85–7.98(d,1H) |
| 11 | 4 | 2-NH(C$_4$H$_9$) | H | 186.5–189° C. (dec.) (DMSO-$d_6$): 0.90–1.10(m,3H) 1.2–1.7(m,4H) 1–3.3(m,2H) 6.53–6.70(dd,1H) 6.98–7.07(d,1H) 6.9–7.6(m,7H) 7.88–8.00(d,1H) |
| 12 | 3 | H | 3-F | 247–250° C. (dec) (DMSO-$d_6$): 6.70–7.60(m,6H); 7.85–8.00(m,1H); 8.64(bs,1H); 9.17(bs,2H); |
| 13 | 4 | H | 3-F | 248–249° C. (dec) (DMSO-$d_6$): 6.70–7.60(m,6H); 8.10–8.22(d,2H); 9.17(bs,1H); 9.37(bs,1H); |
| 14 | 4 | H | 3-Cl | 253–255° C. (dec.) *(DMSO-$d_6$): 7.20–7.80(m,6H) 8.05–8.18(d,2H). |
| 15 | 4 | 2-Br | H | 171–173° C. (dec) (trifluoroacetic acid-d): 7.40(s,5H); 7.90–8.07(dd,1H); 8.45–8.50(d,1H); 8.53–8.67(d,1H). |
| 16 | 4 | 2-Cl | 2-Cl | 208.5° C. (dec.) (DMSO-$d_6$): 7.00–7.80(m,4H); 7.92–7.97(d,1H); 8.00–8.17(dd,1H); 8.37–8.25(d,1H); 8.52(bs,1H); 9.97(bs,1H). |
| 17 | 4 | 2-Cl | 4-Cl | 217° C. (dec.) (DMSO-$d_6$): 7.20–7.60(m,5H) 7.90–7.95(d,1H); 8.23–8.37(d,1H); 9.15(bs,1H); 9.37(bs,1H). |
| 18 | 4 | 2-Cl | 2-F | 191–192° C. (dec) (trifluoroacetic acid-d): 7.10–7.80(m,4H); 7.83–8.00(dd,1H); 8.33–8.38(d,1H); 8.53–8.67(d,1H). |
| 19 | 4 | 2-Cl | 4-F | 187–188° C. (dec) (DMSO-$d_6$): 7.00–7.60(m,5H); 7.90–7.95(d,1H); 8.23–8.35(d,1H); 9.02(bs,1H); 9.33(bs,1H). |
| 20 | 4 | 2-Cl | 2-CH$_3$ | 183–183.5° C. (dec.) (trifluoroacetic acid-d): 2.35(s,3H); 7.37(s,4H); 7.85–8.03(dd,1H); 8.37–8.42(d,1H); 8.48–8.62(d,1H). |
| 21 | 4 | 2-Cl | 3-CH$_3$ | 185–186° C. (dec) (trifluoroacetic acid-d): 2.42(s,3H); 7.00–7.30(bm,4H); 7.87–8.05(dd,1H); 8.38–8.43(d,1H); 8.55–8.68(d,1H). |
| 22 | 4 | 2-Cl | 3-CF$_3$ | 191–191.5° C. (dec.) (trifluoroacetic acid-d): 7.60–7.80(m,4H); 7.87–8.05(dd,1H). |
| 23 | 4 | 2,6-Cl | 3-F | See Example 4 |
| 24 | 4 | 2-CH$_3$ | H | 193–198° C. (dec.) (DMSO-$d_6$): |

TABLE 1-continued

| | | | | |
|---|---|---|---|---|
| 25 | 4 | 3-CH₃ | H | 2.38(s,3H); 6.90–7.70(m,7H); 8.15–8.27(d,1H); 8.92(bs,1H); 9.20(bs,1H).<br>236.5–240° C. (dec)<br>**(DMSO-d₆):<br>(trifluoroacetic acid-d):<br>2.38(s); 7.50(bs); 8.65–8.80(d); 9.12(s); 9.78(s). |
| 26 | 4 | 2-CH₃ | 3-F | See Example 5 |
| 27 | 4 | 2-OCH₃ | H | 213.5–214.5° C. (dec)<br>(trifluoroacetic acid-d):<br>4.33(s,3H); 7.20–7.40(dd) and 7.43(bs,6H); 7.98–8.03(d,1H); 8.13–8.27(d,1H). |
| 28 | 4 | 2-COOCH₃ | H | 213.5–214.5° C. (dec.)<br>(trifluoroacetic acid-d):<br>4.30(s,3H); 7.40(bs,5H); 8.23–8.41(dd,1H); 8.57–8.70(d,1H); 8.83–8.88(d,1H). |
| 29 | 4 | 2-CONH₂ | H | See Example 6 |
| 30 | 4 | 2-N(CH₃)₂ | H | See Example 7, Step A |
| 31 | 4 | 2-N(CH₃)₂ with O | H | See Example 7, Step B |
| 32 | 4 | 2-SCH₃ | H | See Example 8, Step A |
| 33 | 4 | 2-SO₂CH₃ | H | See Example 8, Step B |
| 34 | 4 | 2-S(C₆H₅) | H | 220–221° C. (dec)<br>(trifluoroacetic acid-d):<br>7.20–7.60(m,7H); 7.62(s,5H); 8.23–8.35(d,1H). |
| 35 | 4 | 2-SO₂(C₆H₅) | H | 232° C. (dec.)<br>(trifluoroacetic acid-d):<br>7.50(s,5H); 7.70–8.20(m,5H); 8.27–8.43(dd,1H); 8.50–8.62(d,1H); 8.80–8.85(d,1H). |
| 36 | 4 | 2-S(C₆F₅) | H | 240–242° C. (dec.)<br>(trifluoroacetic acid-d):<br>7.30–7.50(m,6H); 7.83–7.88(d,1H); 8.45–8.57(d,1H). |
| 37 | 4 | 2,6-Cl | H | 213° C. (dec.) |
| 38 | 4 | 2-S-(2,3,4,5-tetrafluorophenyl) | H | 248–249° C. (dec.) |
| 39 | 4 | 2-Cl | 3,5-F | 193–195° C. (dec.) |
| 40 | 4 | 2-(pyridyl)·H₂O | H | 222–223.5° C. (dec.) |
| 41 | 4 | 2-OC₂H₅ | H | 202–203° C. (dec.) |
| 42 | 4 | 2-I | H | 146–150° C. (dec.) |
| 43 | 4 | 2-NHCH₂-C₆H₅ | H | 193–196° C. (dec.) |
| 44 | 4 | 2-OC₃H₇ | H | 206–207° C. (dec.) |
| 45 | 4 | 2-OC₅H₁₁ | H | 162–165° C. (dec.) |
| 46 | 4 | 2,6-Br | H | 193° C. (dec.) |
| 47 | 4 | 2-CH(CH₃)₂ | H | 218–219° C. (dec.) |
| 48 | 4 | 2-SC₂H₅ | H | 228–229° C. (dec.) |
| 49 | 4 | 2-SO₂C₂H₅ | H | 237–239° C. (dec.) |
| 50 | 4 | 2-C₂H₅ | H | 211–213° C. (dec.) |
| 51 | 4 | 2-C₂H₅ | 3-F | 220–221° C. (dec.) |
| 52 | 4 | 2-C₃H₇ | H | 218–219° C. (dec.) |
| 53 | 4 | H | 3,5-F | 257–258° C. (dec.) |
| 54 | 4 | 2-C(CH₃)₃ | H | 203–205° C. (dec.) |
| 55 | 4 | 2-CON(CH₃)₂ | H | 215° C. (dec.) |
| 56 | 4 | 2-C₆H₅ | H | 232–235° C. (dec.) |
| 57 | 4 | 2-NHCH₃ | 3-F | 244–246° C. (dec.) |

TABLE 1-continued

| | | | | |
|---|---|---|---|---|
| 58 | 4 | 2-Cl | 2-OCH₃ | 190–191° C. (dec.) |
| 59 | 4 | 2-Cl | 3-OCH₃ | 183–184° C. (dec.) |
| 60 | 4 | 2-Cl | 2-OH | 185–210° C. (dec.) |
| 61 | 4 | 2-Cl | 3-OH | 240–250° C. (dec.) |
| 62 | 4 | 2-Cl | 4-OH | 200° C. (dec.) |
| 63 | 4 | 2-C₃F₇ | H | 213–215° C. (dec.) |
| 64 | 4 | 2-C₆F₁₃ | H | 204–207° C. (dec.) |
| 65 | 4 | H | 2,3,4-F | 278–279° C. (dec.) |
| 66 | 4 | H | 2,3,4,5,6-F | 254–255° C. (dec.) |
| 67 | 4 | H | 2,4,5-F | 270–272° C. (dec.) |
| 68 | 4 | H | 2,4,6-F | 275–276° C. (dec.) |
| 69 | 4 | H | 2,3,5,6-F | 262–264° C. (dec.) |
| 70 | 4 | 2-Cl | 3-SO₂CH₃ | 212–214° C. (dec.) |
| 71 | 4 | 2-Cl | 2-SO₂CH₃ | 200–201° C. (dec.) |
| 72 | 4 | 2-Cl | 2-SCH₃ | 188–189° C. (dec.) |
| 73 | 4 | 2-Cl | 3-SCH₃ | 183–184° C. (dec.) |
| 74 | 4 | H | 2,3,4,5-F | 258–262° C. (dec.) |
| 75 | 4 | 2,6-CH₃ | 2-F | 257–259° C. (dec.) |
| 76 | 4 | 2,6-CH₃ | 3-F | 256–258° C. (dec.) |
| 77 | 4 | 2,6-CH₃ | 4-F | 257–259° C. (dec.) |
| 78 | 4 | 2-CH₃ | 2-F | 239–240° C. (dec.) |
| 79 | 4 | 2-CH₃ | 4-F | 245–246° C. (dec.) |
| 80 | 4 | 2-CH₃ | 3-F | 249–250° C. (dec.) |

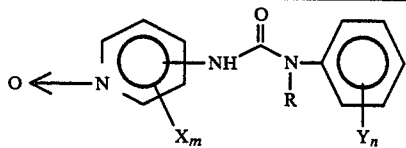

| Cpd. No. | Pyridinyl Position | Xm | Yn | R | Melting Point & NMR |
|---|---|---|---|---|---|
| 81 | 4 | 2-Cl | H | CH₃ | 213° C. (dec.) |
| 82 | 4 | 2-Cl | H | C₂H₅ | 165–167° C. (dec.) |
| 83 | 4 | H | H | CH₃ | 203–205° C. (dec.) |

*Urea protons not visible in NMR spectrum due to poor solubility in solvent.
**Unable to assign protons due to poor spectrum.

TABLE 2

Wheat Leaf Antisenescence (Chlorophyll) Test

| Cpd. No. | % of Zero Value at Stated Concentration | | | |
|---|---|---|---|---|
| | Ctrl | 10⁻⁵ | 10⁻⁷ | 10⁻⁹ |
| 1 | 20 | 52 | 22 | 28 |
| 1 | 10 | 44 | 16 | — |
| 1A | 20 | 28 | — | — |
| 2 | 20 | 32 | 15 | 16 |
| 3 | 20 | 38 | 21 | 21 |
| 4 | 14 | 41 | 18 | 17 |
| 5 | 10 | 29 | 15 | 13 |
| 6 | 8 | 81 | 12 | 6 |
| 6 | 20 | 63 | 31 | 18 |
| 6 | 10 | 77 | 21 | — |
| 6A | 8 | 28 | 7 | 4 |
| 7 | 8 | 79 | 53 | 12 |
| 7 | 15 | 74 | 65 | 28 |
| 7 | 20 | 59 | 60 | 23 |
| 7 | 10 | 87 | 81 | 14 |
| 7 | 10 | 63 | 73 | — |
| 8 | 10 | 78 | 73 | 41 |
| 9 | 10 | 87 | 48 | 19 |
| 12 | 14 | 58 | 13 | 8 |
| 13 | 14 | 76 | 66 | 20 |
| 14 | 16 | 85 | 23 | — |
| 15 | 14 | 76 | 38 | — |
| 16 | 14 | 83 | 63 | — |
| 16A | 14 | 44 | 27 | — |
| 17 | 14 | 48 | 16 | — |
| 18 | 18 | 66 | 36 | — |
| 19 | 18 | 59 | 32 | — |
| 20 | 10 | 81 | 44 | — |
| 20A | 10 | 37 | 21 | — |
| 21 | 10 | 54 | 34 | — |
| 22 | 10 | 52 | 15 | — |
| 23 | 10 | 55 | 24 | — |
| 24 | 16 | 78 | 40 | 20 |
| 24A | 16 | 36 | 31 | — |
| 25 | 10 | 41 | 8 | — |
| 26 | 12 | 78 | 64 | 18 |
| 27 | 10 | 56 | 27 | — |
| 28 | 10 | 61 | 19 | — |
| 29 | 12 | 70 | 30 | — |
| 30 | 21 | 68 | 26 | — |
| 31 | 21 | 61 | 14 | — |
| 32 | 7 | 75 | 14 | — |
| 33 | 7 | 69 | 12 | — |
| 34 | 14 | 52 | 29 | — |
| 35 | 14 | 50 | 20 | — |
| 36 | 7 | 33 | 13 | — |
| 37 | 8 | 70 | 42 | — |
| 37A | 14 | 38 | 25 | 19 |
| 38 | 8 | 72 | 15 | — |
| 39 | 24 | 67 | 66 | — |
| 39 | 21 | 94 | 87 | 46 |
| 40 | 13 | 70 | — | — |
| 41 | 12 | 65 | 19 | — |
| 42 | 12 | 81 | 54 | 16 |
| 42 | 14 | 67 | 48 | — |
| 43 | 16 | 43 | — | — |
| 44 | 21 | 51 | 32 | — |
| 44 | 12 | 73 | 12 | — |
| 45 | 9 | 63 | 17 | — |
| 46 | 16 | 56 | 31 | — |
| 46A | 10 | 33 | 23 | 18 |
| 47 | 16 | 62 | 17 | — |
| 48 | 16 | 67 | 16 | — |
| 49 | 16 | 67 | 19 | — |
| 50 | 9 | 77 | 24 | — |
| 50A | 21 | 47 | — | — |
| 51 | 21 | 68 | 45 | — |
| 52 | 18 | 69 | 12 | — |
| 53 | 10 | 84 | 26 | — |
| 54 | 7 | 8 | 51 | — |

TABLE 2-continued

Wheat Leaf Antisenescence (Chlorophyll) Test

| Cpd. No. | % of Zero Value at Stated Concentration | | | |
|---|---|---|---|---|
| | Ctrl | $10^{-5}$ | $10^{-7}$ | $10^{-9}$ |
| 54 | 0 | 50 | 0 | — |
| 55 | 14 | 61 | — | — |
| 56 | 14 | 63 | — | — |
| 57[a] | 0 | 58 | 0 | — |
| 58 | 0 | 75 | 0 | — |
| 59 | 0 | 58 | 0 | — |
| 60 | 0 | 25 | 0 | — |
| 61 | 0 | 50 | 0 | — |
| 62 | 0 | 42 | 8 | — |
| 63 | 0 | 67 | 0 | — |
| 69 | 0 | 67 | 8 | — |
| 71 | 0 | 50 | 8 | — |
| 75 | 0 | 50 | 0 | — |
| 75 | 0 | 67 | 25 | — |

[a] Antisenescence performance of Compounds 57 through 75 was determined by Antisenescence Test B.

TABLE 3

Soybean Antisenescence Test

| Cpd. No. | % of Zero Value at Stated Concentration | | |
|---|---|---|---|
| | $10^{-5}$ | $10^{-7}$ | $10^{-9}$ |
| 1 | 19 | 58 | 33 | 33 |
| 6 | 21 | 58 | 52 | 24 |
| 7 | 21 | 59 | 64 | 22 |
| 7 | 19 | 50 | 59 | 23 |
| 7 | 25 | 57 | 61 | 47 |
| 7 | 10 | 54 | 51 | 15* |
| 7 | 41 | 65 | 74 | 44 |

*8 day test

TABLE 4

Protein Test

| Cpd. No. | μg Protein/g Fresh Weight at Stated Concentration | | | |
|---|---|---|---|---|
| | Ctrl | $10^{-5}$ | $10^{-6}$ | $10^{-7}$ |
| 1 | 7 | 24 | 24 | 14 |
| 6 | 6 | 38 | | 36 |
| 7 | 14 | 64 | 47 | 47 |
| 7 | 6 | 38 | | 40 |
| 8 | 27 | 158 | 100 | 91 |
| 9 | 27 | 95 | 50 | 26 |
| 10 | 27 | 105 | 69 | 35 |
| 11 | 27 | 67 | 68 | 54 |
| 13 | 24 | 68 | 64 | 49 |
| 14 | 27 | 81 | 74 | 76 |
| 16 | 24 | 90 | 75 | 41 |
| 19 | 27 | 82 | 58 | 52 |
| 24 | 24 | 68 | 56 | 28 |
| 30 | 27 | 60 | 68 | 36 |

TABLE 5

Soybean Senescence Evaluation

| Cpd. No. | Rate (kg/ha) | Plant Growth Stage | Antisenescence at Days Post Trtmt | | | | | | | |
|---|---|---|---|---|---|---|---|---|---|---|
| | | | L | P | L | P | L | P | L | P |
| | | | 20 | | 28 | | 35 | | 42 | |
| 7 | Control | R4 | 3.3 | 5.0 | 2.5 | 2.5 | 1.0 | 1.0 | 0.3 | 1.0 |
| | 0.0625 | | 4.3 | 5.0 | 3.5 | 3.0 | 2.0 | 1.8 | 1.0 | 1.0 |
| | 0.25 | | 4.0 | 5.0 | 3.3 | 3.5 | 1.8 | 1.8 | 0.8 | 1.0 |
| | 1.0 | | 4.8 | 5.0 | 4.0 | 4.0 | 2.5 | 2.0 | 1.5 | 1.3 |
| | Control | R5 | 3.3 | 5.0 | 2.5 | 2.5 | 1.0 | 1.0 | 0.3 | 1.0 |
| | 0.0625 | | 4.0 | 5.0 | 3.8 | 3.8 | 2.3 | 1.8 | 1.0 | 1.0 |
| | 0.25 | | 4.0 | 5.0 | 4.0 | 4.0 | 2.3 | 2.0 | 1.0 | 1.0 |
| | 1.0 | | 5.0 | 5.0 | 4.0 | 4.0 | 3.0 | 2.0 | 1.3 | 1.0 |
| | Control | R6 | 3.3 | 5.0 | 2.5 | 2.5 | 1.0 | 1.0 | 0.3 | 1.0 |
| | 0.0625 | | 4.3 | 5.0 | 4.0 | 4.0 | 2.3 | 2.0 | 1.3 | 1.0 |
| | 0.25 | | 4.0 | 5.0 | 4.0 | 3.8 | 2.8 | 2.0 | 1.3 | 1.0 |
| | 1.0 | | 4.8 | 5.0 | 4.0 | 3.8 | 2.5 | 2.0 | 1.5 | 1.5 |
| | | | 34 | | 41 | | 49 | | 56 | |

TABLE 5-continued

Soybean Senescence Evaluation

| Cpd. No. | Rate (kg/ha) | Plant Growth Stage | Antisenescence at Days Post Trtmt | | | | | | | |
|---|---|---|---|---|---|---|---|---|---|---|
| | | | L | P | L | P | L | P | L | P |
| 8 | Control | R4 | 4.0 | 4.4 | 3.4 | 3.6 | 2.0 | 1.8 | 1.8 | 1.0 |
| | 0.0625 | | 4.0 | 4.8 | 3.0 | 3.4 | 2.2 | 1.6 | 2.2 | 1.0 |
| | 0.25 | | 3.8 | 4.4 | 3.6 | 3.6 | 2.6 | 2.0 | 3.0 | 1.0 |
| | 1.0 | | 4.2 | 4.8 | 3.8 | 3.8 | 2.8 | 2.0 | 2.6 | 1.0 |
| | | | 20 | | 28 | | 35 | | 42 | |
| | Control | R5 | 3.8 | 4.6 | 2.0 | 3.0 | 1.4 | 1.4 | 0.4 | 1.0 |
| | 0.0625 | | 4.0 | 4.8 | 3.0 | 3.2 | 2.2 | 1.8 | 1.0 | 1.0 |
| | 0.25 | | 4.4 | 4.8 | 3.0 | 3.6 | 2.0 | 2.0 | 1.6 | 1.0 |
| | 1.0 | | 4.8 | 4.8 | 3.8 | 3.6 | 2.8 | 2.6 | 2.6 | 1.0 |
| | | | 22 | | 29 | | 36 | | | |
| 10 | Control | R4 | 3.8 | 5.0 | 3.0 | 4.4 | 1.2 | 1.2 | | |
| | 0.125 | | 3.8 | 5.0 | 3.4 | 4.4 | 2.0 | 1.6 | | |
| | 0.5 | | 4.2 | 5.0 | 3.2 | 4.6 | 1.6 | 1.6 | | |
| | 2.0 | | 4.0 | 5.0 | 2.8 | 4.0 | 1.6 | 1.4 | | |
| | | | 21 | | 28 | | 36 | | 56 | |
| | Control | R5 | 4.4 | 4.8 | 3.2 | 4.0 | 2.4 | 3.4 | 0.8 | 1.0 |
| | 0.125 | | 4.4 | 5.0 | 3.6 | 5.0 | 3.2 | 3.8 | 1.2 | 1.0 |
| | 0.5 | | 4.4 | 5.0 | 3.6 | 4.8 | 2.8 | 3.6 | 1.0 | 1.0 |
| | 2.0 | | 5.0 | 5.0 | 4.0 | 4.8 | 3.0 | 3.8 | 1.0 | 1.0 |
| | | | 34 | | 41 | | 49 | | 56 | |
| 13 | Control | R4 | 4.2 | 4.8 | 2.4 | 2.8 | 1.2 | 1.2 | 0.8 | 1.0 |
| | 0.0625 | | 4.2 | 4.8 | 2.2 | 3.5 | 2.4 | 2.0 | 1.2 | 1.0 |
| | 0.25 | | 4.2 | 5.0 | 2.6 | 3.0 | 2.0 | 2.0 | 1.2 | 1.0 |
| | 1.0 | | 4.4 | 5.0 | 2.8 | 3.4 | 2.6 | 2.0 | 1.6 | 1.0 |
| | | | 20 | | 27 | | 35 | | 45 | |
| | Control | R5 | 4.2 | 4.8 | 2.2 | 3.4 | 2.0 | 2.0 | 0.8 | 1.0 |
| | 0.0625 | | 4.0 | 4.8 | 2.0 | 3.2 | 1.8 | 1.8 | 0.8 | 1.0 |
| | 0.25 | | 4.4 | 5.0 | 2.4 | 3.8 | 2.2 | 2.0 | 0.8 | 1.0 |
| | 1.0 | | 4.6 | 5.0 | 3.2 | 4.0 | 2.8 | 2.0 | 1.6 | 1.0 |
| | | | 21 | | 28 | | 35 | | 43 | |
| 15 | Control | R4 | 4.2 | 5.0 | 4.2 | 4.8 | 3.2 | 4.2 | 2.2 | 2.8 |
| | 0.125 | | 4.6 | 5.0 | 4.6 | 5.0 | 3.6 | 4.2 | 3.0 | 3.4 |
| | 0.5 | | 4.8 | 5.0 | 5.0 | 5.0 | 4.4 | 5.0 | 3.6 | 4.0 |
| | 2.0 | | 4.6 | 5.0 | 4.8 | 5.0 | 4.6 | 5.0 | 3.8 | 4.0 |
| | | | 21 | | 28 | | 36 | | 42 | |
| | Control | R5 | 4.6 | 5.0 | 3.4 | 4.4 | 3.2 | 3.4 | 0.8 | 1.0 |
| | 0.125 | | 4.4 | 5.0 | 4.0 | 4.8 | 3.6 | 4.2 | 1.4 | 1.2 |
| | 0.5 | | 5.0 | 5.0 | 4.0 | 5.0 | 4.4 | 4.8 | 3.0 | 2.2 |
| | 2.0 | | 4.8 | 5.0 | 4.0 | 5.0 | 4.0 | 4.6 | 3.0 | 2.8 |

TABLE 5A

Soybean Utility Test (Var. Williams)

| Cpd. No. | Rate (kg/ha) | Plant Growth Stage | Harvest | | | |
|---|---|---|---|---|---|---|
| | | | No. of Pods | No. of Seeds | 100 Seed wt (gm) | Total Seed wt (gm) |
| 7 | Control | R4 | 124.3 | 286.3 | 17.2 | 49.7 |
| | 0.0625 | | 118.3 | 299.5 | 20.4 | 61.6 |
| | 0.25 | | 110.3 | 265.0 | 20.5 | 54.8 |
| | 1.0 | | 105.5 | 252.3 | 20.9 | 53.5 |
| | Control | R5 | 124.3 | 286.3 | 17.2 | 49.7 |
| | 0.0625 | | 125.8 | 299.8 | 19.6 | 59.5 |
| | 0.25 | | 116.0 | 285.3 | 20.2 | 57.4 |
| | 1.0 | | 122.8 | 303.3 | 18.2 | 57.5 |
| | Control | R6 | 124.3 | 286.3 | 17.2 | 49.7 |
| | 0.0625 | | 131.8 | 306.8 | 19.3 | 59.5 |
| | 0.25 | | 113.5 | 276.5 | 20.2 | 56.1 |
| | 1.0 | | 114.8 | 285.3 | 20.1 | 57.5 |
| 8 | Control | R4 | 86.8 | 213.6 | 22.7 | 47.2 |
| | 0.0625 | | 93.2 | 215.0 | 24.3 | 51.4 |
| | 0.25 | | 89.2 | 199.4 | 23.8 | 46.1 |
| | 1.0 | | 92.8 | 204.4 | 23.3 | 46.0 |
| | Control | R5 | 75.6 | 192.8 | 19.0 | 37.4 |
| | 0.0625 | | 89.0 | 215.0 | 21.2 | 44.3 |
| | 0.25 | | 81.4 | 184.2 | 22.9 | 41.9 |
| | 1.0 | | 88.6 | 193.6 | 24.3 | 45.3 |
| 10 | Control | R4 | 63.2 | 155.0 | 19.4 | 30.1 |
| | 0.1255 | | 67.6 | 174.8 | 19.2 | 33.5 |
| | 0.5 | | 60.4 | 148.4 | 20.1 | 29.9 |
| | 2.0 | | 57.6 | 145.6 | 19.9 | 28.6 |
| 13 | Control | R4 | 102.8 | 254.4 | 19.4 | 48.7 |
| | 0.0625 | | 93.0 | 226.0 | 21.9 | 48.6 |
| | 0.25 | | 84.0 | 209.8 | 21.1 | 44.6 |

TABLE 5A-continued

Soybean Utility Test (Var. Williams) Harvest

| Cpd. No. | Rate (kg/ha) | Plant Growth Stage | No. of Pods | No. of Seeds | 100 Seed wt (gm) | Total Seed wt (gm) |
|---|---|---|---|---|---|---|
| | 1.0 | | 91.6 | 225.4 | 21.3 | 47.4 |
| | Control | R5 | 84.8 | 209.6 | 21.0 | 43.4 |
| | 0.0625 | | 89.2 | 219.2 | 21.6 | 46.8 |
| | 0.25 | | 90.0 | 222.4 | 20.8 | 46.1 |
| | 1.0 | | 80.2 | 184.2 | 22.1 | 40.3 |

TABLE 6

Turf Reduction Test of Compound 7 (Bluegrass)

| Rate (kg/ha) | Number Of Treatments[a] | Grass Height (cm)[b] | |
|---|---|---|---|
| | | 41-Days | 71-Days |
| Control | 1 | 18.5 | 17.6 |
| 0.25 | | 16.3 | 15.5 |
| 0.5 | | 15.4 | 14.9 |
| 1.0 | | 14.2 | 16.5 |
| 2.0 | | 13.0 | 14.9 |
| Control | 2 | 16.4 | 16.5 |
| 0.25 | | 16.6 | 17.4 |
| 0.5 | | 13.8 | 15.4 |
| 1.0 | | 13.1 | 13.9 |
| 2.0 | | 11.8 | 14.6 |

[a] One treatment: Mature bluegrass was cut to 1" above pot rim then sprayed with appropriate solution. Two treatments: After one week half of the one treatment pots were resprayed with the corresponding solution.
[b] Average of 5 replicates.

We claim:

1. A compound of the formula

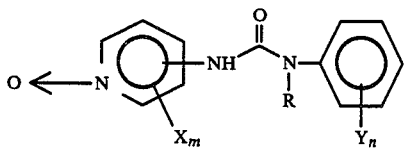

in which R is hydrogen or a lower alkyl group; and
(a) the pyridinyl ring is attached at position 4; each X group is independently selected from halogen, $(C_{1-4})$alkyl, $(C_{1-5})$alkoxy, $(C_{1-6})$haloalkyl, $(C_{1-2})$alkoxycarbonyl, aminocarbonyl, $(C_{1-4})$alkylamino, di$(C_{1-2})$alkylamino, di$(C_{1-2})$alkylaminocarbonyl, di$(C_{1-2})$-alkylamino-N-oxide, $(C_{1-2})$alkylthio, $(C_{1-2})$alkylsulfonyl, pyridinyl, phenylthio, phenylsulfonyl, phenyl, or benzylamino in which the aromatic ring is in turn unsubstituted or substituted with 1 to 5 halogen atoms; each Y group is independently selected from halogen, $(C_{1-2})$alkyl, $(C_{1-2})$alkoxy, $(C_{1-2})$alkylthio, $(C_{1-2})$alkylsulfonyl, hydroxyl, or trihalomethyl; m is 0, 1 or 2; and n is 0 to 5; or
(b) the pyridinyl ring is attached at position 3; X is chloro, methoxy, or an acetylmethylamino group; Y is halogen; m is 0 or 1; and n is 0 or 1.

2. A compound of claim 1 in which the pyridinyl ring is attached at position 4.
3. A compound of claim 1 in which Y is hydrogen.
4. A compound of claim 2 in which X is hydrogen, halogen, $(C_{1-2})$alkyl, or $(C_{1-2})$alkylthio.
5. A compound of claim 4 in which Y is hydrogen, halogen, $(C_{1-2})$alkyl of $(C_{1-2})$alkoxy; and n is 0, 1 or 2.
6. N-(3-chlorophenyl)-N'-(2-chloro-4-pyridinyl-N-oxide)urea, a compound of claim 5.
7. N-(3-chlorophenyl)-N'-(4-pyridinyl-N-oxide)urea, a compound of claim 5.
8. N-(2-chlorophenyl)-N'-(2-chloro-4-pyridinyl-N-oxide)urea, a compound of claim 5.
9. N'-(2-chloro-4-pyridinyl-N-oxide)-N-(2-methylphenyl)urea, a compound of claim 5.
10. N'-(2-chloro-4-pyridinyl-N-oxide)-N-(3,5-difluorophenyl)urea, a compound of claim 5.
11. N-(3,5-difluorophenyl)-N'-(4-pyridinyl-N-oxide)urea, a compound of claim 5.
12. N'-(2-iodo-4-pyridinyl-N-oxide)-N-phenylurea, a compound of claim 5.
13. N-phenyl-N'-(4-pyridinyl-N-oxide)urea, a compound of claim 5.
14. N'-(2-chloro-4-pyridinyl-N-oxide)-N-phenylurea, a compound of claim 5.
15. N'-(2-chloro-4-pyridinyl-N-oxide)-N-3-fluorophenyl)urea, a compound of claim 5.
16. N'-(2-methyl-4-pyridinyl-N-oxide)-N-phenylurea a compound of claim 5.
17. N'-(2-ethyl-4-pyridinyl-N-oxide)-N-phenylurea, a compound of claim 5.
18. N'-(2-ethylthio-4-pyridinyl-N-oxide)-N-phenylurea, a compound of claim 5.
19. [N-(2-chlorophenyl)-N'-(4-pyridinyl-N-oxide)]ethylurea, a compound of claim 5.
20. A plant growth regulator composition comprising a plant regulating amount of a compound of claim 1 in admixture with an agriculturally acceptable carrier or extender.
21. A method for retarding senescence in wheat or soybean plants which comprises applying to the plant a plant regulating amount of a compond of claim 1.
22. A method for improving leaf abscision of cotton for harvesting which comprises applying to cotton plants a defoliating amount of the compound of claim 1.

* * * * *